United States Patent

Anis

[11] Patent Number: 5,222,959
[45] Date of Patent: Jun. 29, 1993

[54] REMOVAL OF TISSUE

[76] Inventor: Aziz Y. Anis, 9540 Firethorne La., Lincoln, Nebr. 68520

[21] Appl. No.: 553,975

[22] Filed: Jul. 17, 1990

[51] Int. Cl.⁵ .............................................. A61B 17/32
[52] U.S. Cl. .................................... 606/107; 606/180
[58] Field of Search ............... 604/22; 606/107, 159, 606/167, 180

[56] References Cited

U.S. PATENT DOCUMENTS

| | | | |
|---|---|---|---|
| 3,882,872 | 5/1975 | Douvas et al. | 606/107 |
| 3,976,077 | 8/1976 | Kerfoot, Jr. | 606/107 |
| 3,990,453 | 11/1976 | Douvas et al. | 606/107 |
| 3,996,935 | 12/1976 | Banko | 604/22 |
| 4,167,943 | 9/1979 | Banko | 604/22 |
| 4,320,761 | 3/1982 | Haddad | 606/107 |
| 4,445,509 | 5/1984 | Auth | 606/159 |
| 4,819,635 | 4/1989 | Shapiro | 604/22 |
| 4,867,157 | 9/1989 | McGurk-Burleson et al. | 606/180 |
| 4,886,061 | 12/1989 | Fischell et al. | 604/22 |
| 4,895,560 | 1/1990 | Papantonakas | 606/159 |
| 4,909,249 | 3/1990 | Akkas et al. | 606/107 |
| 5,024,652 | 6/1991 | Dumenek et al. | 604/22 |
| 5,030,201 | 7/1991 | Palestrant | 604/27 |

Primary Examiner—Stephen C. Pellegrino
Assistant Examiner—Ralph A. Lewis
Attorney, Agent, or Firm—Vincent L. Carney

[57] ABSTRACT

To reduce damage to surrounding tissue while fragmenting some tissue such as for example not damaging the capsular wall while removing the lens during cataract removal surgery or not damaging artery or vein walls during bypass surgery while freeing the artery or vein to be transplanted, an incision is made for the insertion of surface-discriminating fragmenting handpiece. The surface-discriminating fragmenting handpiece fragments and permits aspiration of the tissue without damaging the surrounding wall by moving surfaces which permit the diseased tissue to fall within their cutting zone but which move at a rate of speed and have openings between them of such a size that the more integrated and smoother tissue does not fall within their cutting zone.

3 Claims, 4 Drawing Sheets

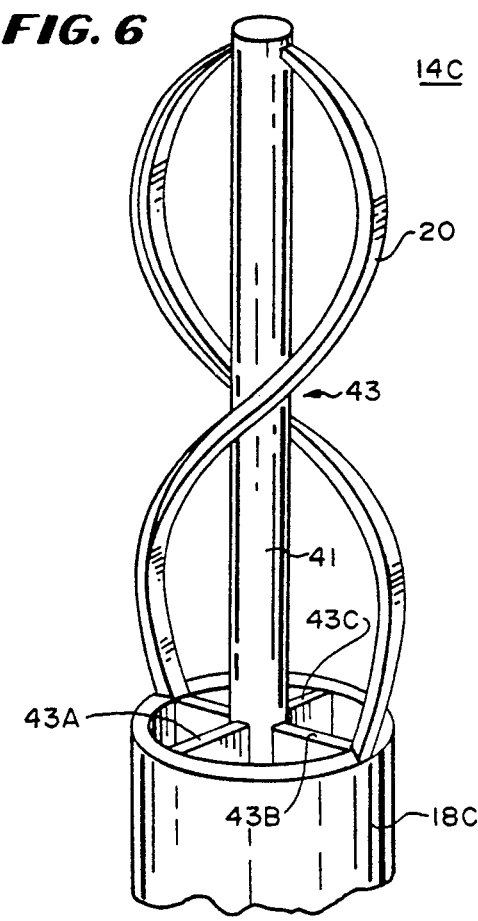
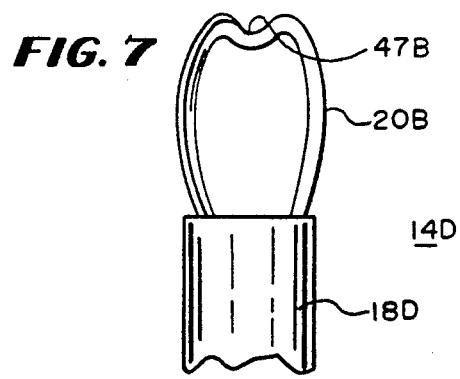
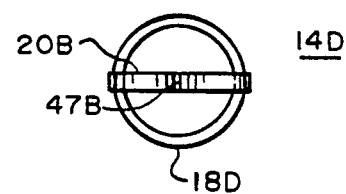
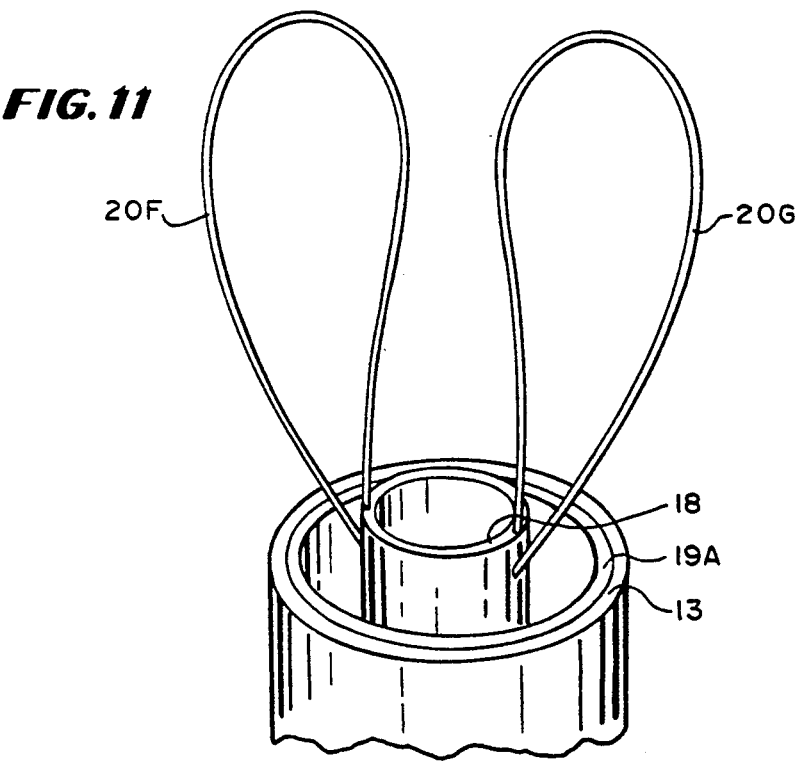

REMOVAL OF TISSUE

BACKGROUND OF THE INVENTION

This invention relates to the removal of tissue from the body such as for example removal of cataracts from the eye.

It is known to remove diseased tissue from the body by fragmenting, crushing or otherwise making the tissue flowable while in the body and then aspirating it. In one prior art surgical technique specifically for the removal of cataracts: (1) an incision is made along the superior corneal margin from about 10 to 2 o'clock (12 o'clock is the location closest to the top of the head of the patient) approximately 10 mm in chord length; (2) an incision is made in the capsular wall; and (3) the cataract is removed. The anterior chamber is maintained substantially formed during the operation by means of a continuous inflow of irrigating solution.

In one prior art technique, for removing a cataract, the nucleus is expressed out of the eye and the cortex is removed by a process of irrigation and aspiration.

In another prior art technique for removing the cateract, the nucleus is removed with a vectis and about 0.1 milliliter of viscoelastic compound or irrigating fluid is introduced into the capsular bag to separate the capsular walls. With the capsular walls separated, a wedge of the cortex is engaged in the aspiration port of a cannula and peeled toward the center and then aspirated to remove it behind the anterior capsule within the capsular cavity.

This process is repeated so that the layers of the cortex are peeled and then aspirated inwardly through the cannula layer by layer until the intact capsular bag (except for the horizontal incision) is completely empty and clean. This technique of removing the cataract is disclosed by Anis, Aziz Y., "Illustrated Step-by-Step Description of the Anis Dry Extra Capsular Cataract Extraction Technique With In-the-Bag Lens Implementation"; *Seminars in Opthalmology*, v. 1, N. 2 (June), 1986, pp. 113-129.

Two prior art types of instruments which aid in the fragmentation and aspiration of the lens nucleus to permit extraction through a small incision are disclosed in U.S. Pat. No. 3,589,363 to Anton Banko et al.; U.S. Pat. No. 3,902,495 to Steven N. Weiss; U.S. Pat. No. 3,693,613 to Charles Kelman et al.; and U.S. Pat. No. 4,041,947 to Steven N. Weiss et al. This instrument is intended in the prior art to fragment a lens nucleus using ultrasonic sound to aid the irrigation/aspiration of the lens. The ultrasonic vibrations laterally reciprocate the tip of an instrument to fracture the cataract after which it can be aspirated.

A further type of instrument, not prior art, is U.S. Pat. No. 4,908,015 issued to Anis on Mar. 13, 1990. This patent describes a prior art instrument which rotates a solid member having blades extending from it to grind the lens.

These prior art removal techniques have several disadvantages, such as: (1) they risk tearing the capsular wall with ultrasonic vibration tools or with the rotating blades; (2) they intentionally make large incisions in or remove parts of the capsular wall; and (3) they may require several instruments and are inconvenient to use.

Still another type of prior art technique for removing cataracts is disclosed in U.S. Pat. No. 3,996,935 to Banko issued Dec. 14, 1976. This type of instrument shows cooperating jaw-like members, one of which rotates inside the other to break up the lens by shearing sections of it. It aspirates fragments through the instrument. This type of instrument has a disadvantage in that it can break the capsular wall and is relatively complex. Part of the disadvantage comes from the teaching that it may be rotated manually or mechanically without a corresponding teaching of the rate of rotation required for efficient use.

SUMMARY OF THE INVENTION

Accordingly, it is an object of the invention to provide a novel technique for tissue removal.

It is a further object of the invention to provide a novel instrument for fragmenting and removing a cataract during cataract removal surgery with low risk of damage to the capsular wall.

It is a still further object of the invention to provide an instrument designed to fragment tissue without damage to the nearby tissue such as for example not damaging the capsular wall while removing the lens during cataract removal surgery or not damaging artery or vein walls while removing cancerous tissue near the vein or artery.

In accordance with the above and further objects of the invention, an incision is made for the insertion of a surface—discriminating fragmenting handpiece. The surface—discriminating fragmenting handpiece fragments and permits aspiration of the tissue without damaging nearby smooth walls. It avoids fragmenting the smooth walls with its cutting edges but slices through rougher tissue, fragmenting it and moving it into a negative pressure zone for aspiration.

The surface discrimination of the instrument is controlled by moving surfaces which permit the diseased tissue to fall within their cutting zone but which move at a rate of speed and have openings between them of such a size that the more integrated and smoother tissue does not fall within their cutting zone. The surfaces are not constrained by opposed shear forces of the instrument but are free to move and the cutting edge of the instrument cuts tissue that: (1) is stiffer and has a higher modulus of rigidity; and (2) is at an angle to the cutting edge closer to 90 degrees and receives less force moving it away. Thus, the surgeon removing a cataract adjusts the speed of movement of the cutting edge to cut cortex within a higher modulus and more projections in the path of the cutting surface and not the capsular wall with a lower modulus and fewer projections closer to 90 degrees so it is more readily moved away from the cutting edge. The aspiration pressure is more effective within the sphere of the rotating tip. It is low enough to pull the fragmented tissue but not the smooth wall. The rotating surfaces move the smooth wall outwardly and provide some counter pressure to the aspirating pressure inside the cutting zone. In one embodiment, radially inwardly extending teeth further fragment and mix tissue within the cutting zone.

In the case of cataract removal surgery, a small incision of 2 to 7 millimeters and preferably 3 millimeters is made in the sclera along the corneal border at 12 o'clock and another incision of similar dimension or a round hole in the anterior capsular wall. The instrument is inserted and fragments the rougher lens matter without fragmenting the capsular wall.

In the preferred embodiment, the surface-discriminating fragmenting handpiece includes a shaft with an aspirating port in it within the cutting zone of a rotating ring or loop. The cutting zone has cutting edges which fragment the lens or other tissue as they rotate are separated by open spaces into which the lens is moved as the rotation occurs to cut into it. The rotation is at a sufficient speed and the area of the open spaces between the cutting edges sufficiently small so that relatively smooth intact tissue such as the capsular wall does not extend into the cutting surfaces because the cutting surfaces move it away with their non-cutting surface which close the opening leading to the cutting zone with great frequency during the rotation while permitting projections on the rougher portions of the lens to be fragmented.

The actual time that the cutting zone should be open to fragment tissue without injuring healthy smooth walls differs from eye to eye or tissue to tissue and may be selected in accordance with the surgeon's observations prior to use. It is a function of the stiffness and smoothness of the capsular wall or other healthy smooth tissue, the hardness and length of projections of the lens or other diseased or projecting tissue and the aspirating pressure necessary to draw fragments out of the eye.

In a preferred embodiment, a zone of a sphere having a diameter of 2 millimeters with the sphere having open spaces about the solid zone (ring shaped or toroidal) is rotated at approximately 12,000 rpm (revolutions per minute). The solid zone is preferably approximately 0.50 millimeter wide along the surface of the sphere. In another embodiment, the solid zone is approximately 0.75 milimeters wide leaving an open area of slightly less than 9 square millimeters and more precisely 8.9 square millimeters with a length of 2.4 millimeters at the longest circle of a segment. The distance should be less than 5 millimeters and have an area less than 10 square millimeters. The time between portions of the solid zone sweeping across any surface is approximately every 25 milliseconds and should be no longer than every 300 milliseconds (1,000 rpm), but may be as short as 75 microseconds (400,000 rpm).

With this arrangement and with parameters adjustable for the particular circumstance, the capsular wall does not enter into the cutting zone within the sphere and may be scrubbed but is not cut through if the rotating surfaces contact the capsular wall and yet it is able to fragment the lens for easy aspiration.

Although the preferred embodiment is a zone of a sphere and intended for use within an eye, other shapes may be used and the instrument has other uses such as in vascular operations. For example, cylinders may be used or multiple zones of a sphere may be spaced from each other at a shorter distance so that the item need not be rotated as fast and motion other than rotational motion may be used to prevent entrance of the tissue into the cutting zone. A convenient embodiment for removing structures around veins or arteries during vascular, operations is dumbell shaped so that a recess fits around the vein while spherical cutting zones are positioned on either side of the vein.

In some embodiments, the moving surface is formed of a curved member attached to a rotatable shaft having a sharpened edge at an angle of between 0 and 60 degrees but preferably 45 degrees with the surface of an imaginary sphere or spheres which sphere or spheres have a center of rotation line with the rotating shaft. The sharpened edge of the curved member faces inwardly toward the center of rotation so that the cutting action of the sharpened surface is inwardly such as for example into the cortex and core material of a cataract rather than outwardly toward the casular wall. The shaft may be rotated by a small electric motor or the like. However, the sharp cutting edge can face outwardly if the speed of rotation is increased to avoid cutting the capsule. It is rotated at a speed so that the movement of the surface cuts the relatively stiff cellular projections of the cortex and nucleus but not the smoother more flexible capsular wall.

As can be understood from the above description, the technique and instrument of this invention have several advantages, such as: (1) they selectively fragment some tissue without damaging other nearby tissue; and (2) they are able to fragment, mix and aspirate tissue and in the case of cataract removal, also scrub the capsular wall without damaging it, all with one instrument.

SUMMARY OF THE DRAWINGS

The above noted and other features of the invention will be better understood from the following detailed description when considered with reference to the accompanying drawings, in which:

FIG. 6 is still another embodiment of blade portion which may be used instead of the embodiments of FIGS. 4 and 5 as substitutes for the blade portion in the embodiment of FIG. 1;

FIGS. 7 and 8 are elevational and plan views respectively of another embodiment of blade portion.

FIG. 11 is a perspective view of still another embodiment of blade portion;

DETAILED DESCRIPTION

Figure 1:
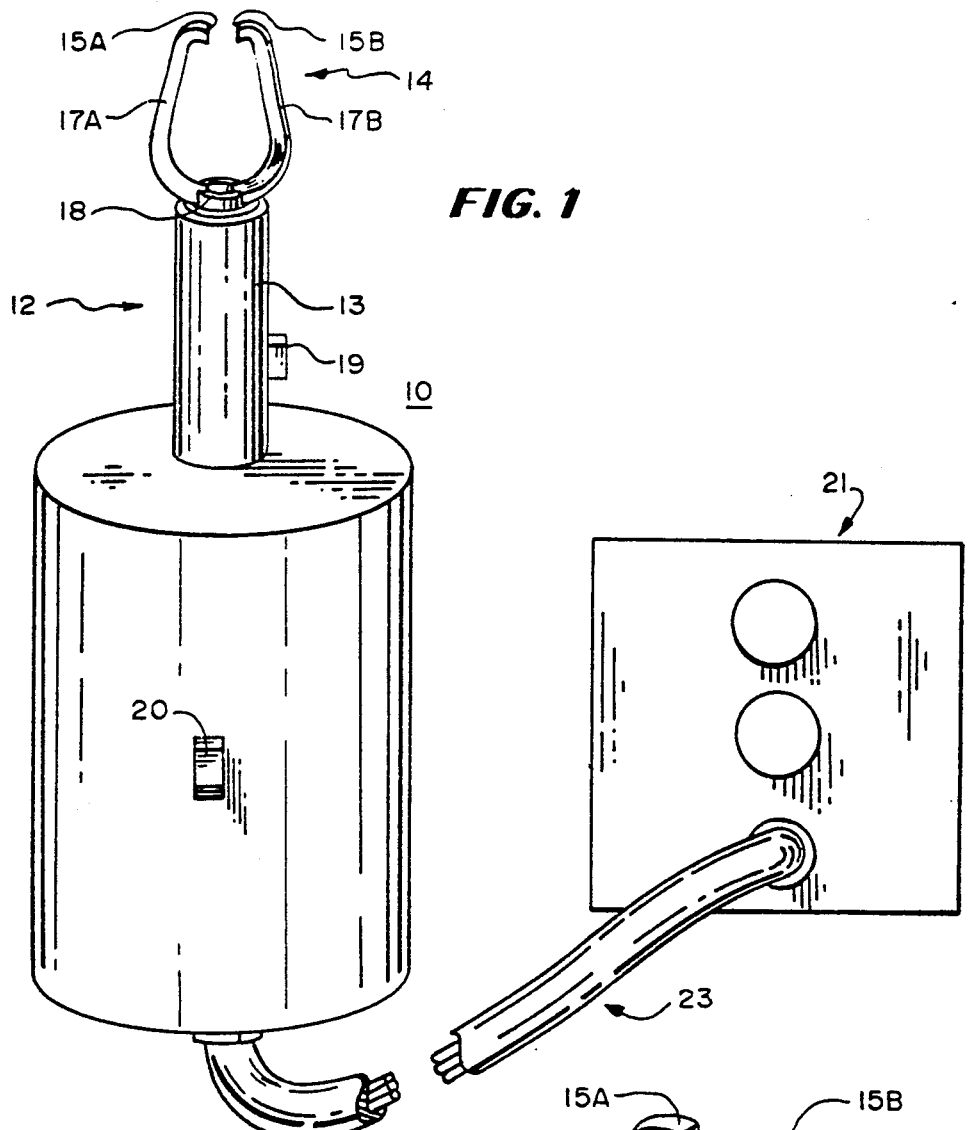
FIG. 1 is a simplified elevational view of a handpiece and control console for fragmenting and removing cataracts in accordance with an embodiment of the invention.

In FIG. 1, there is shown an elevational view of a surface-discriminating fragmenting handpiece 10, connecting tubing 23 and a console 21. The handpiece 10 includes a blade portion 14 and a tubular handle portion 12. The tubular handle portion 12 includes a tubular casing 13, an on-off switch 20 and an inner tabular shaft 18.

The blade portion 14 includes blades 17A and 17B each of which is fastened to the rotatable tubular shaft 18 at diametrically opposite locations and each of which has a corresponding one of the blunt tips 15A and 15B turned inwardly to avoid cutting. The outer sleeve 13 includes within it a movable sleeve (not shown in FIG.

1) so that upon longitudinal movement of the button 19 and the outer casing 13 of the tubular handle portion 12 with respect to each other, the blades 17A and 17B move apart in a fragmenting position in one direction and upon movement in the other direction are forced within movable sleeve within the tubular handle 12 against the pressure of the spring like blades to fit within a smaller incision such as a 2 millimeter opening. The blades 17A and 17B are wider in the direction of rotation to resist bending but flat to bend outwardly under centrifugal force and from their own resiliency during use.

With this arrangement, the blades 17A and 17B may be moved together for insertion of the handpiece 10 into the capsular sack through a relatively small aperture and then permitted to expand outwardly so that the upon rotation of the blade section 14 the cortex and nucleus are fragmented within the capsular sack. In the embodiment of FIG. 1, the handpiece 10 includes a motor for rotating the shaft and a tubular connector 23 for aspirating fragments. The console 21 may include for cooperation with the handpiece 10, a standard source of electrical power, a vacuum source, a source of aspirating liquid and a pump for aspirating liquid. These elements are conventional and are not part of the invention except insofar as they cooperate with the handpiece 10.

Figure 2:
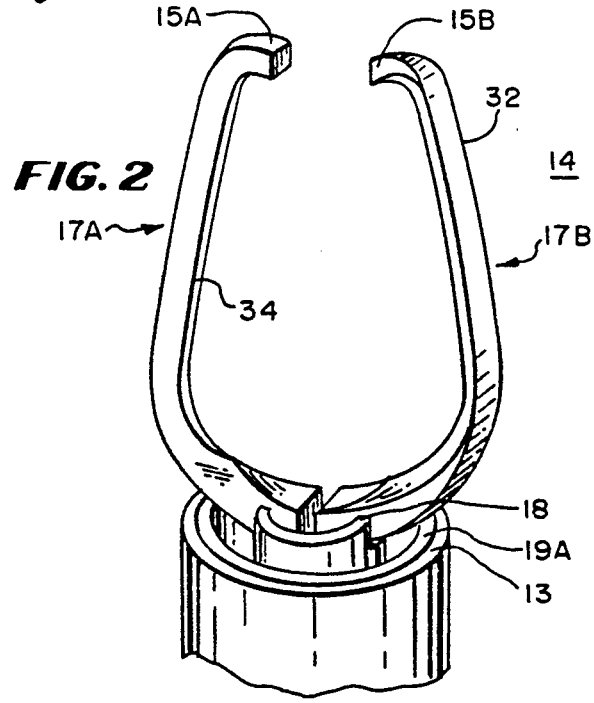
FIG. 2 is an enlarged perspective view of a portion of the embodiment of FIG. 1.

In FIG. 2, there is shown an enlarged fragmentary perspective view of the blade assembly 14 first and second blades 17A and 17B with corresponding blunt tips 15A and 15B. The blades 17A and 17B are sufficiently flexible in the embodiment of FIG. 2 to expand until they form outwardly curved cutting surfaces extending beyond the surfaces of shaft 13 and have sharpened edges 32 and 34 tangentially to or pointing inwardly from the circles of rotation formed as they rotate. When the blades 17A and 17B are pulled inwardly, they fit within a cylinder having a diameter of less than 2 millimeters.

While the embodiment of FIGS. 1 and 2 have blades with sharpened edges pointing tangentially to or inwardly from the direction of rotation, sharpened edges are not necessary and the angle of attack of the sharpened edges when they are part of an embodiment may vary. However, the angle of attack is from tangential to 60 degrees inwardly of the rotation and preferably 45 degrees.

To permit compressing of the blades 17A and 17B into a protective sleeve, the tubular handle portion 12 includes three coaxial sleeves 18, 19A and 13 in that order outwardly from the central axis. The blades are mounted to tubular sleeve 18 for rotation therewith and there is a space between sleeves 18 and 19A for irrigating fluid to flow. The sleeve 19A is affixed to the button 19 (FIG. 1) and moveable axially with respect to sleeves 18 and 13 to slide over the blades 17A and 17B and compress them inwardly.

Figure 3:
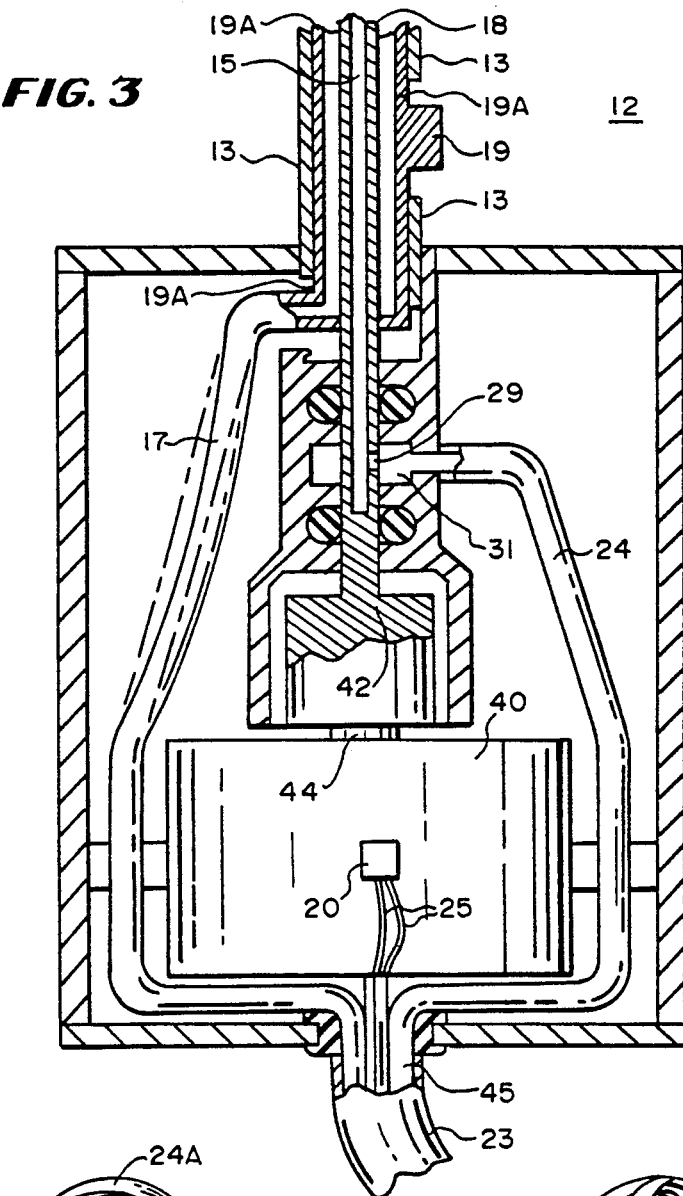
FIG. 3 is a fragmentary sectional view of another portion of the embodiment of FIG. 1.

In FIG. 3, there is shown a broken away longitudinal sectional view of the handle 12 having within it the tubular shaft 18, the tubular aspirating sleeve 19A, the outer sleeve 13, a motor 40 for rotating the shaft 18 to turn the blades 17A and 17B, (FIG. 1) the hollow aspirating tube 24, an irrigating tube 17 and electrical wires 25. The shaft 18 is coupled at one end 42 to the output shaft of 44 of the motor 40 for rotation therewith and to the tubular connection 45 for aspiration.

As shown in this view, the outer wall 13 supports within it a solid movable wall 19A with a button extending through a slot in the outer wall 13 by which the wall 19A may be moved upwardly and downwardly to bend the blades 17A and 17B inwardly for retraction or permit them to expand outwardly in the cutting position to their normal position for rotating and in some embodiments still further under centifugal force when rotating. However, the moment of inertia of the blades is sufficient so that the centrifugal force does not force the points to point outwardly and only the bent flat surface is presented to the outer wall during rotation. It is spaced from the movable tube 19 to permit irrigating fluid to flow therebetween and contains in its center the opening 15 which extends downwardly for aspiration of tissues.

To provide irrigating fluids, the conduit 17 is connected through the cable 23 to the console 21 (FIG. 1) from which irrigating liquid is pumped through the conduit 17 around the motor 40 and to the space between the movable tube 19 and shaft 18 to supply irrigating fluid to the capsular sack. To aspirate tissue, the central opening 15 in the shaft 18 passes through an opening 29 in the wall of the shaft 18 and communicates through the sealed circular ring 31 with the aspirating conduit 25. The conduit 25 passes around the motor 40 and through the cable 23 to the console 21 which applies slight negative pressure to aspirate tissue. The cable 23 also carries electrical conductors for the motor 40 which are connected in series between the switch 20, and a source of electrical power in the console 21 and the motor 40.

To use the embodiment of FIGS. 1-3, an incision is made for the insertion of the surface-discriminating fragmenting handpiece 10. The surface-discriminating fragmenting handpiece 10 fragments and permits aspiration of the tissue but avoids damaging nearby smooth walls. Instead it slices rougher surfaces such as those having projections. This surface discrimination is controlled by the moving surface of the blades 17A and 17B which permit the diseased tissue to fall within their cutting zone but which move at a rate of speed and have openings between them of such a size that the more integrated and smoother tissue does not fall within their cutting zone. The aspirating pressure and turbulence is counteracted or attenuated within the sphere of the rotating ring to avoid damage to the flat surface tissue.

In the case of cataract removal surgery, a small incision of 2 to 7 millimeters and preferably 3 millimeters in the sclera along the corneal border at 12 o'clock and another incision of similar dimensions in the capsular wall. The instrument is inserted and fragments the rougher lens without fragmenting the capsular wall.

The actual time that the cutting zone must be open to fragment diseased tissue without injuring smooth walls differs from eye to eye or tissue to tissue and may be selected in accordance with the surgeon's observations prior to use. It is a function of the stiffness and smoothness of the capsular wall or other healthy tissue, the hardness or length of projections of the lens or other diseased tissue and the aspirating pressure necessary to draw fragments out of the eye or other location.

In a preferred embodiment, a ring or a zone of a rotating sphere having a diameter of 2 millimeters with the sphere having open spaces about the solid zone (ring shaped or toroidal) is rotated at approximately 12,000 rpm (revolutions per minute). The solid zone is approximately 0.50 millimeter wide along the surface of the sphere, leaving an open area of slightly less than 9 square millimeters and more precisely 8.9 square millimeters with a length of 2.4 millimeters at the longest circle of a segment. The time between portions of the solid zone sweeping across any surface is approximately every 25 milliseconds and should be no larger than every 300 milliseconds (1,000 rpm) but may be as short as 75 micrseconds (400,000 rpm).

With this arrangement and with parameters adjustable for the particular circumstance, the capsular wall does not enter into the cutting zone within the sphere and may be scrubbed but is not cut through if the rotating surfaces contact the capsular wall and yet it is able to fragment the lens for easy aspiration. The motion of the moving surfaces neutralize the negative pressure of aspiration or create outward centrifugal pressure on objects outside of the cutting zone but projective and loose particles are swept into the cutting zone and aspirating.

Figure 4:
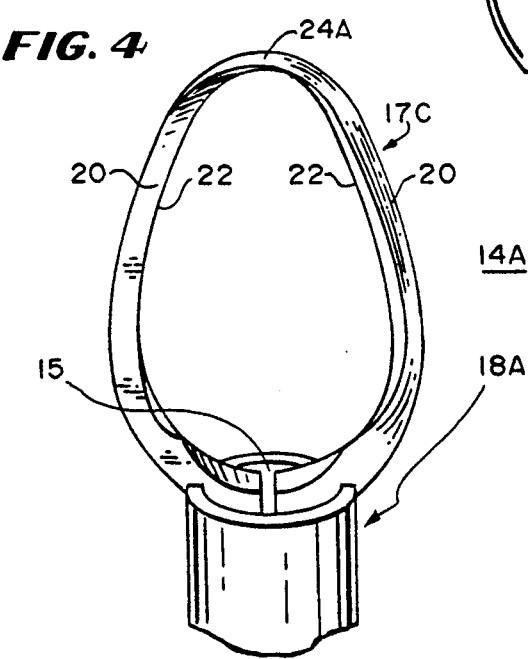
FIG. 4 is a fragmentary perspective view of another embodiment of blade portion usable as a replacement for the blade portion in the embodiment of FIG. 1.

In FIG. 4, there is shown a second embodiment of blade portion 14A having a shaft 18A connected to a blade 17C formed as a partial zone of a circle or an arc extending from the shaft 18 and being flexible with the blade portions turned at a 45 degree angle so as to have: (1) blunt outer edges 20; (2) sharpened inner edges 22 at a 45 degree angle with the wall of a sphere having its center along the axis of the rod 18A; and (3) transition points 24 along the axis of the tube 18 so that there is always a blunt outer edge with a sharpened inner edge facing inwardly as the cutting blade rotates about the shaft 18A. It has been found tht even sharpened edges in the tangential place or outward of the tangential plane do not rupture the outer capsular wall if rotation is at the proper speed but preferably the sharpened edge makes an angle with a tangent to the circle of rotation of the blade 17C of between zero and 95 degrees and points in a direction away from the surface. In the embodiment of FIG. 4, the blades do not extend beyond the wall 19A (FIG. 3) and bending force is not required to move them inwardly. Moreover, centrifugal force does not substantially distort the shape of the blades. They may be thick enough to resist distortion.

Figure 5:
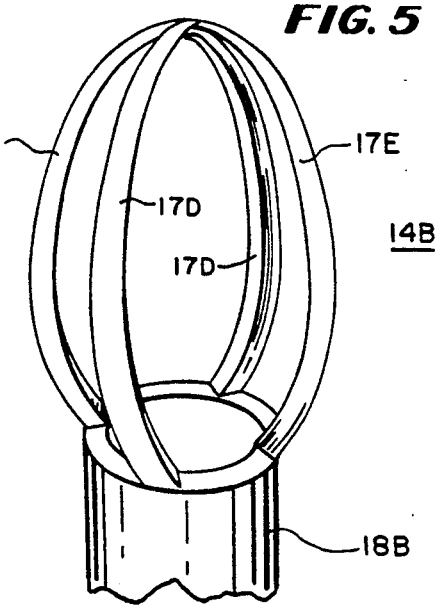
FIG. 5 is still another embodiment of blade portion useful in the embodiment of FIG. 4.

In FIG. 5, there is shown a longitudinal elevational view of an embodiment of blade portion 14B having a plurality of cutting members such as those shown at 17D and 17E mounted to the single shaft 18B within the tubular handle 12 (FIG. 3) similar to those of the embodiment of FIG. 4. The shaft 18B is adapted to be rotated by the battery operated motor 40 in the same manner as the embodiment of FIGS. 1-3.

In FIG. 6, there is shown another embodiment of blade portion 14C having a tube 18C and flexible blades 20 formed of a continuous flexible ribbon like material bent so that its blades are at a 45 degree angle to the surface of spheres positioned adjacent to each other with a blunt edge outwardly in a manner similar to that of the embodiment of FIG. 4 and supported by post 41. This arrangement is mounted similarly to the embodiment of FIG. 4. However, it is particularly suited for vascular work where it may be positioned with the vein or artery at 43 for freeing it of connecting tissue.

For support, the blade 20 is mounted to the post 41 which in turn is supported by the webs 43A-43C and fastened at the top and middle at 43 to prevent distortion. The webs 43A-43C extend radially between the post 41 and tube 18C and are thin enought to permit aspiration through the shaft 18C.

In FIGS. 7 and 8, there are shown elevational and top views of still another embodiment of blade portion 14D having a blade 20B shaped with a depression 47B forming two arched portions at its upper end facing in the direction of the tubular shaft 18D and rotating thereabout to permit it to provide a center area outside of the cutting zone in the forward direction for positioning at a point which it not to be cut and cutting around that point for fragmenting and aspirating. This embodiment operates substantially the same as the prior embodiments except that its unique shape enables careful placement for special purposes.

Figure 9:
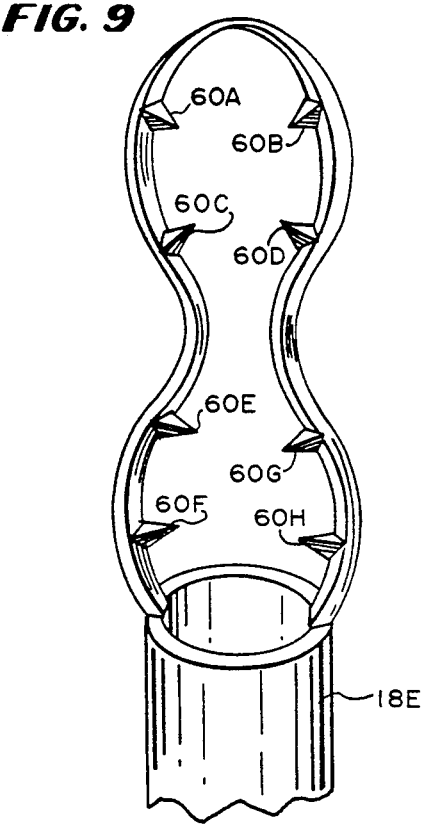
FIG. 9 is a perspective view of still another embodiment of blade portion.

In FIG. 9, there is shown a simplified perspective view of still another embodiment of blade portion 14E having cutting surfaces 20 formed substantially as a FIG. 8 with a depressed portion 43A so that the surfaces of rotation form a dumbell shape with a central section which may fit over a vein or artery or other object while the rotating surfaces on either side of it remove rough tissue. This embodiment, may include several surfaces rotating together such as illustrated by the above embodiments and other changes in their shape. Moreover, this embodiment as well as others may include inwardly projecting teeth such as those shown at 60A-60F which serve to further fragment and mix material within the cutting zone for better aspiration.

Figure 10:
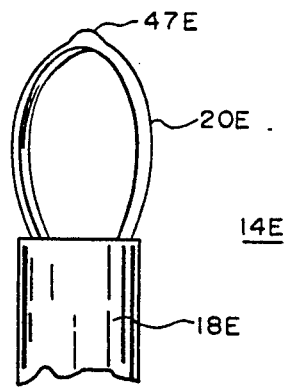
FIG. 10 is a perspective view of still another embodiment of blade portion.

In FIG. 10, there is shown a simplified fragmentary perspective view of another embodiment of blade portion 20E having a cutting portection 47E with side cutting members capable of drilling into and enlarging openings.

In FIG. 11, there is shown a simplified fragmentary perspective view of a retractable blade embodiment similar to that of FIGS. 1-3 except that two wire-like blades 20F and 20G having one end fastened to the end of rotatable tube 18 and the other extending downwardly for pulling or pushing to enlarge or narrow the blade portion loops on each side of the outer tube 13.

Figure 12:
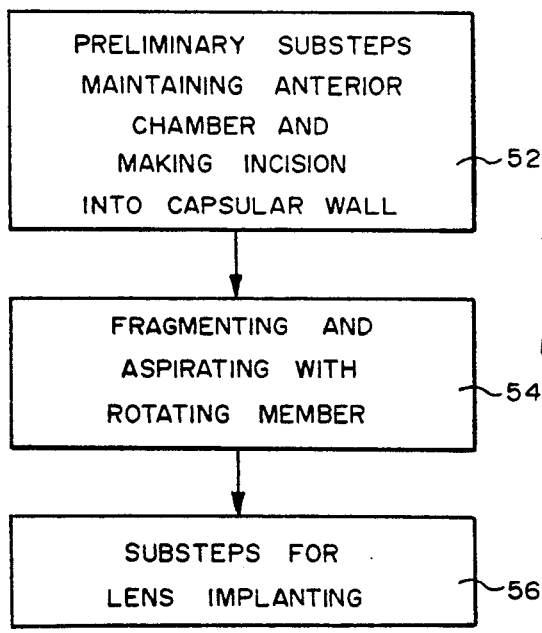
FIG. 12 is a block diagram of a process for using the instrument of FIGS. 1 through 6 to remove a cataract.

In FIG. 12, there is shown a block diagram generally illustrating the steps in a cataract extraction and lens implantation technique 50 comprising: (1) the step 52 which includes the preliminary substeps of maintaining the anterior chamber and making the incision into the capsular wall; (2) the step 54 of fragmenting and removing the lens; and (3) the step 56 which includes the substeps necessary for implanting the lens.

In performing this technique, the step 52 which includes the substeps required to make the incision and maintain the anterior chamber and the step 56, which includes the substeps necessary for implanting are not by themselves new and many of the steps are described in Anis, Aziz Y., "Illustrated Step-by-Step Description of the Anis Dry Extra Capsular Cataract Extraction Technique With In-the-Bag Lens Implementation", *Seminars in Opthalmology*, v. 1, N. 2 (June), 1986, pp. 113-129. Moreover, the removal of the lens may not be followed by implantation but may be part of a treatment in which the aphakia is treated by contact lens or glasses.

The step 54 of fragmenting and removing the lens includes: (1) the step of inserting the handpiece; (2) the step of extending the blades in some embodiments within the capsular bag; and (3) the step of breaking and removing the hardened part of the nucleus. These steps are all performed through a small incision while the anterior chamber is maintained with a viscoelastic medium. Hydrodelineation may be performed as described in U.S. Pat. No. 4,908,015, if desired, but such hydrodelineation is not part of this invention.

The step 52 which includes preliminary substeps of maintaining the anterior chamber and making the incision in the capsular bag includes the substep of making a small incision in the capsular bag, preferably no greater than 3 millimeters in length and in the range of 1 to 2 millimeters. This incision is made while the anterior chamber is maintained and is made as small as possible to maintain the structure of the capsular bag to the extent possible. Through this small incision, the step 54 of fragmenting and removing the lens and the step 56 of implanting a lens are performed. Under some circumstances, the incision may be 4 or 5 millimeters but should always be less than 7 millimeters.

Figure 13:
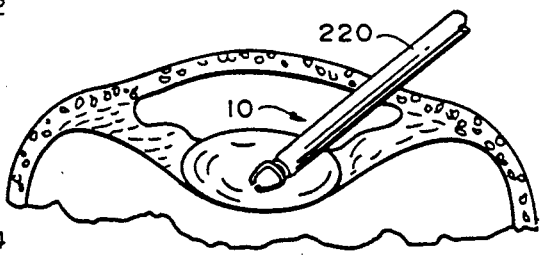
FIG. 13 is a simplified cross-sectional view of eye and cataract removal handpiece tip illustrating a portion of the technique of this invention.

With the posterior capsule in focus in the focal plane of the microscope, the handpiece 10 is introduced through an incision shown at 220 in FIG. 13 in the wall of the capsulary sac. The tip of a handpiece 10 is thrust through the incision in the wall of the capsular bag and into the lens therein.

In using one embodiment of handpiece as shown in FIGS. 1-3 and 11, the wall 19A is pulled downwardly to extend the blades 17A and 17B or 17F and 17G. In other embodiments, the blades already extend outwardly and are ready for use. The blades are rapidly rotated while slight pressure is applied to aspirate the fragments. The rotating blades are inserted gradually into the cortex and nucleus and from time to time a small amount of irrigating fluid is injected. Fragmented cotex or nucleus is aspirated. After removal of the cataract and the handpiece with the capsular sac relatively intact, a lens implant is inserted through a relatively small opening as described in the above publication of Anis.

Generally, the nucleus is first removed then the cortex. The surface—discriminating fragmenting handpiece fragments and permits aspiration of the cotex and nucleus without damaging nearby smooth walls of the capsular sac. It avoids fragmenting the smooth walls with its cutting edges but slices through rougher tissue, fragmenting it and moving it into a negative pressure zone for aspiration. The smooth surface is swept by the blades which hit it at an angle with the cellular stiffer projections extending 5 micrometers or more are cut.

The surface discrimination of the instrument is controlled by moving surfaces which permit the diseased tissue to fall within their cutting zone but which move at a rate of speed and have openings between them of such a size that the more integrated and smoother tissue does not fall within their cutting zone. The surfaces are not constrained by opposed shear forces of the instrument but are free to move and the cutting edge of the instrument cuts tissue that: (1) is stiffer and has a higher modulus of rigidity; and (2) is at an angle to the cutting edge closer to 90 degrees and receives less force moving it away. Thus, the surgeon removing a cataract adjusts the speed of movement of the cutting edge to cut cortex with a higher modulus and more projections in the path of the cutting surface and not the capsular wall with a lower modulus and fewer projections closer to 90 degrees so it is more readily moved away from the cutting edge. On the other hand, the fibrous cortex and the nucleus with roughness of projections extending the apiration pressure is more effective within the sphere of the rotating tip. It is low enough to pull the fragmented tissue but not the smooth wall. The rotating surfaces move the smooth wall outwardly and provide some counter pressure to the aspirating pressure inside the cutting zone. In one embodiment, radially inwardly extending teeth further fragment and mix tissue within the cutting zone.

As can be understood from the above description, the technique and equipment of this invention has several advantages, such as: (1) they selectively fragment some tissue without damaging other nearby tissue; and (2) they are able to fragment, mix and aspirate tissue and in the case of cataract removal also scrub the capsular wall without damaging it, all with one instrument.

Although a preferred embodiment of the invention has been described with some particularity, many modifications and variations are possible in the preferred embodiment without deviating from the invention. Therefore, it is to be understood that within the scope of the appended claims, the invention may be practiced other than as specifically described.

What is claimed is:

1. A method comprising the steps of:

inserting a surface discriminating fragmenting tip through small opening in the eye into the lens of an eye wherein the tip has movable spaced apart cutting surfaces;

moving the cutting surfaces at a rate high enough so that smooth healthy tissue does not move into the space between cutting edges but slow enough so that rougher tissue containing projections are moved into a cutting zone; whereby the rougher tissue is pulverized;

aspirating the pulverized material;

making a small incision in the capsular sac along the margin to make the small opening;

the step of moving the cutting surfaces including the step of inserting a fragmenting tip and rotating the fragmenting tip to fragment a cataract;

retracting the cutting surfaces of said fragmenting tip when inserting the fragmenting tip;

releasing said cutting surfaces when the fragmenting tip is inside the capsular sac; and retracting said cutting surfaces when removing the fragmenting tip, whereby a small incision may be used.

2. A method comprising the steps of:

making a small incision in the capsular sac of an eye along the margin to make a small opening;

inserting a surface discriminating fragmenting tip through the small opening in proximity with the lens of the eye, wherein the surface discriminating fragmenting tip has two movable spaced-apart elongated cutting blades, curved inwardly from a first diameter to a second smaller diameter at the tip and having an open space at the tip with the small diameter;

rotating the movable spaced-apart cutting surfaces with the cutting edges of the blades positioned to contact a lens and a capsular wall of the capsular sac without being constrained by opposed shear forces of edges of the surface discriminating fragmenting tip;

adjusting the rate of rotation of the cutting blades to a rate that fragments cortex that has a modulus sufficiently high to prevent the portion swept by the edge to move away from the path of cutting edges of the cutting blades and not the capsular wall that has a modulus of elasticity sufficiently low to permit the capsular wall to move from the path of the edge and avoid fragmenting wherein the fragmenting is only caused by the cutting blades without the aid of shear forces between an edge of the blade and another portion of the surface discriminating tip;

aspirating the pulverized material; and introducing irrigating fluid into the capsular sac.

3. A method in accordance with claim 2 in which the step of rotating the movable spaced-apart cutting surfaces comprises the step of rotating the movable spaced-apart cutting surfaces with the tubular portion at a rate so that the cutting surfaces sweep across the smooth healthy tissue once during a time period of between 75 microseconds and 25 milliseconds.

* * * * *